United States Patent [19]

Maywald et al.

[11] Patent Number: 5,276,160
[45] Date of Patent: Jan. 4, 1994

[54] PREPARATION OF 3-CARBAMOYLISOXAZOLE-4-CARBOXYLIC ESTERS BY SELECTIVE AMIDATION

[75] Inventors: Volker Maywald, Ludwigshafen; Thomas Kuekenhoehner, Boehl-Iggelheim; Gerhard Hamprecht, Weinheim, all of Fed. Rep. of Germany

[73] Assignee: BASF Aktiengesellschaft, Ludwigshafen, Fed. Rep. of Germany

[21] Appl. No.: 35,660

[22] Filed: Mar. 23, 1993

[30] Foreign Application Priority Data

Mar. 26, 1992 [DE] Fed. Rep. of Germany ....... 4209849

[51] Int. Cl.$^5$ .......................................... C07D 261/08
[52] U.S. Cl. ............................................ 548/248
[58] Field of Search .................................. 548/248

[56] References Cited

U.S. PATENT DOCUMENTS

5,001,124  3/1991  Patterson et al. .................. 548/248

FOREIGN PATENT DOCUMENTS

3931627  9/1989  Fed. Rep. of Germany ...... 548/248

Primary Examiner—Mary C. Lee
Assistant Examiner—Joseph K. McKane
Attorney, Agent, or Firm—Keil & Weinkauf

[57] ABSTRACT

Abstract of the Disclosure: 3-Carbamoylisoxazole-4-carboxylic esters of the formula I

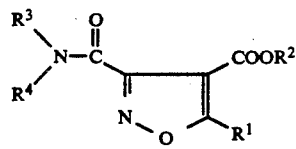

where
 $R^1$ is hydrogen, alkyl, cycloalkyl, phenyl or a 5- to 6-membered heterocyclic radical, it being possible for the organic radicals to carry substituents which are inert under the reaction conditions;
 $R^2$ is alkyl, cycloalkyl, benzyl or $C_1$–$C_3$-alkenyl;
 $R^3$ is hydrogen, alkyl or cycloalkyl and
 $R^4$ is an aliphatic or cycloaliphatic radical or unsubstituted or substituted phenyl, or $R^4$ together with $R^3$ is a 4- to 7-membered alkylene chain which can be interrupted by oxygen, sulfur or N-methyl, are prepared by selective amidation of an isoxazole-3,4-dicarboxylic diester of the formula II

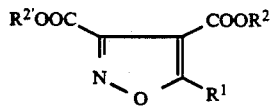

where $R^{2'}$ has the meanings of $R^2$ and is identical to or different from $R^2$.

5 Claims, No Drawings

PREPARATION OF 3-CARBAMOYLISOXAZOLE-4-CARBOXYLIC ESTERS BY SELECTIVE AMIDATION

The present invention relates to the preparation of 3-carbamoylisoxazole-4-carboxylic esters of the formula I

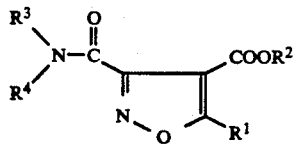

where
- $R^1$ is hydrogen, alkyl, cycloalkyl, phenyl or a 5- to 6-membered heterocyclic radical, it being possible for the organic radicals to carry substituents which are inert under the reaction conditions;
- $R^2$ is alkyl, cycloalkyl, benzyl or $C_3$-$C_6$-alkenyl;
- $R^3$ is hydrogen, alkyl or cycloalkyl and
- $R^4$ is an aliphatic or cycloaliphatic radical or unsubstituted or substituted phenyl, or $R^4$ together with $R^3$ is a 4- to 7-membered alkylene chain which can be interrupted by oxygen, sulfur or N-methyl.

3-Carbamoylisoxazole-4-carboxylic acid derivatives sort out spacing I are intermediates for organic syntheses, in particular for preparing crop protection agents (cf. DE-A-39 31 627).

It is an object of the present invention to find a process of maximum simplicity and economy for synthesizing the compounds I.

We have found that this object is achieved by a process for preparing 3-carbamoylisoxazole-4-carboxylic esters I, which comprises selective amidation at position 3 of an isoxazole-3,4-dicarboxylic diester of the formula II

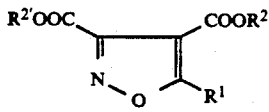

where $R^{2'}$ has the same meanings as $R^2$ and is identical to or different from $R^2$, with a primary or secondary amine of the formula III

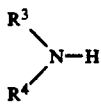

where $R^3$ and $R^4$ have the abovementioned meanings, in the presence or absence of a solvent.

The process according to the invention is attractive owing to its simplicity, and it was by no means predictable that it would be successful because there are two identical functional groups on the isoxazole system II, both of which ought to react with the amine III.

We have found, surprisingly, that the amidation takes place virtually exclusively at position 3. The corresponding isoxazole-4-carboxamide derivatives IV

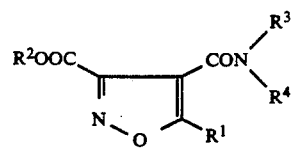

and the isoxazole-3,4-dicarboxamides V

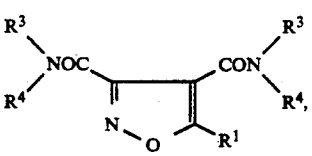

which were expected to be formed in considerable amounts in the reaction according to the invention, are formed to only negligible extent, if at all, under the reaction conditions used.

It is possible by the process according to the invention to convert the isoxazole-3,4-dicarboxylic diesters II with virtually all primary and secondary amines of the formulae IIIA ($R^3$=H) and IIIb ($R^3 \neq$ H)

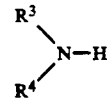

selectively into the corresponding 3-carbamoylisoxazole-4-carboxylic esters II.

In the amines III which are preferably employed, $R^3$ is hydrogen, $C_1$-$C_6$-alkyl, especially $C_1$-$C_4$-alkyl such as methyl, ethyl, propyl, isopropyl, butyl, isobutyl, secbutyl, tert-butyl and $C_3$-$C_6$-Cycloalkyl such as cyclopropyl, cyclobutyl, cyclopentyl and cyclohexyl, especially cyclopropyl, and $R^4$ is unsubstituted or substituted alkyl, cycloalkyl, alkenyl or alkynyl. Examples of $R^4$ are: $C_1$-$C_6$-alkyl, especially $C_1$-$C_4$-alkyl as mentioned for $R^3$, which can be substituted by cyclopropyl, halogen such as fluorine, chlorine or bromine, cyano or $C_1$-$C_6$-alkoxy, or $C_3$-$C_6$-cycloalkyl which can be substituted by $C_1$-$C_4$-alkyl or halogen, or $C_3$-$C_6$-alkenyl or $C_3$-$C_6$-alkynyl. Furthermore, amines III which are preferably used are those in which $R^3$ and $R^4$ together form a $C_4$-$C_7$-methylene chain which can be interrupted by oxygen, sulfur or N-methyl.

It is particularly preferred, both in view of the intended use and from the industrial process viewpoint, to react the isoxazole-3,4-dicarboxylic diesters II with simple primary aliphatic amines such as methylamine, ethylamine, propylamine, isopropylamine, butylamine, isobutylamine, sec-butylamine, (R)-sec-butylamine, (S)-sec-butylamine, tert-butylamine, neopentylamine and 1,1-dimethylpropylamine, substituted primary aliphatic amines such as 1-cyclopropylethylamine, (R)-1-cyclopropylethylamine, (s)-1-cyclopropylethylamine and cyclopropylmethylamine, cycloalkylamines such as cyclopropylamine, cyclobutylamine, cyclopentylamine, cyclohexylamine and 1-methylcyclopropylamine, unsaturated amines such as 2-propenylamine, 1-methyl-2-propenylamine, 1,1-dimethyl-2-propenylamine, 2-propynylamine, 1-methyl-2-propynylamine and 1,1-dimethyl-2-propynylamine, simple secondary amines such as dimethylamine, methylethylamine, diethylamine, dipropylamine, dibutylamine, methylisopropylamine, diisopropylamine and methyl-tertbutylamine, and cyclic secondary amines such as pyrrolidine, piperidine and morpholine.

The amine III can be employed in the stoichiometric amount as well as in virtually any molar excess relative to the reactant II. However, the molar amount of amine III is advantageously from 1 to 8 times, in particular from 1 to 5 times, that of the diester. It may, however, also be advantageous to add the amine III to the compound II in such a way that the isoxazole-3,4-dicarboxylic diester II is in excess relative to the amine III virtually throughout the reaction.

The process according to the invention is particularly preferably carried out by using the amine III in excess relative to the isoxazole-3,4-dicarboxylic diester II for the amidation, in which case the excess amine III itself acts as solvent.

The reaction according to the invention can, where appropriate, be carried out in a solvent which is inert under the reaction conditions. Solvents which are preferably used are ethers such as diethyl ether, diisopropyl ether, methyl tert-butyl ether, dimethoxyethane, diethylene glycol dimethyl ether, tetrahydrofuran or dioxane, halohydrocarbons such as dichloromethane, chloroform or chlorobenzene, aromatic hydrocarbons such as benzene, toluene or xylene, and sulfoxides such as dimethyl sulfoxide or sulfolane. Alcohols are particularly preferred solvents, for example alkanols or cycloalkanols such as n-butanol, isobutanol, tert-butanol, glycol, glycerol, n-propanol, isopropanol, amyl alcohol, cyclohexanol, 2-methyl-4-pentanol, ethylene glycol monoethyl ether, 2-ethylhexanol, methylglycol and, in particular, ethanol and reethanol. It is, of course, also possible to use mixtures of solvents.

It is expedient to employ an amount of solvent which is from 0.5 to 10 times, preferably from 1 to 5 times, the weight of II.

In the process according to the invention, the isoxazole-3,4-dicarboxylic diester II starting material is reacted with the amine III at from 0° to 100° C. particularly preferably from 20° to 80° C. It is expedient to carry out the reaction of amines which are not sterically hindered at from 20° to 60° C., whereas that of amines III with one or two sterically demanding substituents R and $R^4$ is generally carried out at higher temperatures, in particular from 60° to 100° C.

The process according to the invention is generally carried out under atmospheric pressure. However, it may also be particularly advantageous, depending on the nature of the amine or solvent used, to carry out the reaction under elevated pressure, especially under autogenous pressure in an autoclave. This measure leads to advantageous results especially when low-boiling amines iii such as methylamine, ethylamine, isopropylamine or cyclopropylamine, or low-boiling solvents such as diethyl ether or methanol are used. It is also, of course, possible for the process according to the invention to be carried out under pressure which has been elevated by external means, expediently in the range from 1 to 50 bar.

The amidation can be carried out in a conventional manner either batchwise in stirred vessels or autoclaves or continuously in cascades of stirred vessels or tubular reactors. Overall, the process requires no special techniques so that further information on this is unnecessary. The reaction is generally complete after from 1 to 20 hours, depending on the conditions such as pressure and temperature and depending on the starting compounds. Since the required isoxazole-3-carboxamide derivatives are formed with high selectivity in the process according to the invention, it is sufficient in many cases merely to remove the solvent and/or the excess amine III by distillation to obtain a product I which is sufficiently pure for further processing. However, it is also possible to work up the reaction mixture in a conventional way by extracting the excess amine with dilute aqueous acids, and isolating the product I from the organic phase. This procedure is particularly preferred when the amine III to be removed is relatively involatile.

In view of the intended use of the isoxazole derivatives I, $R^1$ and $R^2$ in the 3-carbamoylisoxazole-4-carboxylic esters I formed by the process according to the invention from the corresponding isoxazole-3,4-dicarboxylic diesters of the formula II preferably have the following meanings:

$R^1$ hydrogen, lower alkyl such as $C_1-C_6$-alkyl, especially $C_1-C_4$-alkyl such as methyl, ethyl, propyl, isopropyl, butyl, isobutyl, sec-butyl or tert-butyl, which can be substituted by from one to three halogen atoms such as fluorine, chlorine, bromine or iodine, especially fluorine and chlorine, one $C_1-C_3$-alkoxy radical such as methoxy, ethoxy, propoxy or isopropoxy, especially methoxy, or one $C_3-C_6$-cycloalkyl radical such as cyclopropyl, cyclobutyl, cyclopentyl or cyclohexyl, especially cyclopropyl, cycloalkyl such as $C_3-C_6$-cycloalkyl, eg. cyclopropyl, cyclobutyl, cyclopentyl, cyclohexyl, cycloheptyl or cyclooctyl, especially cyclopropyl, which can be substituted one to three times by $C_1-C_4$-alkyl as mentioned above, especially methyl, a 5- to 6-membered saturated, unsaturated or aromatic heterocyclic radical containing one or two hetero atoms selected from the group comprising oxygen, sulfur and nitrogen, such as 2-tetrahydrofuranyl, 3-tetrahydrofuranyl, 2-tetrahydrothienyl, 3-tetrahydrothienyl, 2-tetrahydropyranyl, 3-tetrahydropyranyl, 4-tetrahydropyranyl, 2-furanyl, 3-furanyl, 2-thienyl, 3-thienyl, 3-isoxazolyl, 4-isoxazolyl, 5-isoxazolyl, 2-oxazolyl, 4-oxazolyl, 5-oxazolyl, 2-thiazolyl, 4-thiazolyl, 5-thiazolyl, 2-pyridyl, 3-pyridyl or 4-pyridyl, which can be substituted by $C_1-C_3$-alkyl as mentioned above, especially methyl, $C_1-C_3$-alkoxy as mentioned above, especially methoxy, or halogen such as fluorine, chlorine, bromine or iodine, especially fluorine and chlorine;

phenyl which can carry f rom one to three of the following groups: $C_1-C_4$-alkyl as mentioned above, especially methyl, $C_1-C_4$-haloalkyl, especially trifluoromethyl, $C_1-C_4$ -alkoxy, especially methoxy, $C_1-C_4$-haloalkoxy, especially trifluoromethoxy, halogen as mentioned above, especially fluorine and chlorine, nitro and cyano;

$R^2$ and $R^2$ $C_1-C_4$-alkyl as mentioned for $R^1$, especially methyl and ethyl, $C_3-C_6$-cycloalkyl as mentioned for $R^1$, especially cyclohexyl, benzyl and $C_3-C_6$-alkenyl, especially allyl.

EXAMPLES

Examples of methods for the selective reaction of dialkyl isoxazole-3,4-dicarboxylates II with mines III

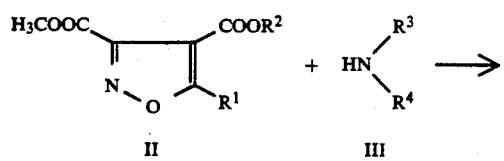

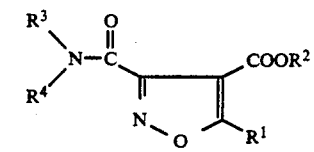

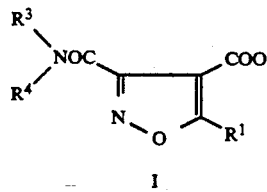

(a) in the presence of a solvent
(b) in the absence of a solvent (a) 0.6 mol of cyclopropylamine is added dropwise to a solution of 0.3 mol of dialkyl 5-alkylisoxazole-3,4-dicarboxylate I in 100 ml of dry alcohol at 25° C., and the mixture is then stirred at room temperature for 12 h. After the reaction is complete, the excess cyclopropylamine and the solvent are stripped off under reduced pressure. Other primary or secondary amines can be reacted in a similar manner. The experimental results are compiled in the Table.

TABLE

| Example No. | $R^1$ | $R^2$ | $R^3$ | $R^4$ | Solvent | Yield (%) | M.p. [°C.]; $^1$H-NMR (CDCl$_3$); 250 MHz; δ in ppm |
|---|---|---|---|---|---|---|---|
| 1 | Me | Me | H | cyclo-Pr | MeOH | 74 | 0.60–0.92(m, 4H); 2.70(s, 3H); 2.93(m, 1H); 3.92(s, 3H); 8.27(bs, 1H, NH) |
| 2 | Et | Me | H | cyclo-Pr | MeOH | 93 | 0.58–0.95(m, 4H); 1.34(t, 3H); 2.93(m, 1H); 3.10(q, 2H); 3.92(s, 3H); 7.95(bs, 1H, NH) |
| 3 | iPr | Me | H | cyclo-Pr | MeOH | 87 | 0.60–0.93(m, 4H); 1.36(d, 6H); 2.92(m, 1H); 3.70(sp, 1H); 3.89(s, 3H); 7.84(bs, 1H, NH) |
| 4 | iPr | Et | H | cyclo-Pr | EtOH | 85 | 0.60–0.90(m, 4H); 1.36(d, 6H); 1.37(t, 3H); 2.93(m, 1H); 3.73 (sp, 1H); 4.35(q, 2H); 7.75(bs, 1H, NH) |

Me = methyl, Et = ethyl, Pr = propyl (b) 32.0 g (0.15 mol) of dimethyl 5-ethylisoxazole-3,4-dicarboxylate and 44.3 g (0.75 mol) of methylethylamine are heated in a 300 ml miniautoclave at 600° C. for 6 hours. The reaction mixture is then concentrated in a rotary evaporator, taken up in ether and extracted twice with 50 ml of 1N HCl each time. The organic phase is dried over magnesium sulfate, and the solvent is stripped off under reduced pressure. 30.1 g (84%) of methyl 5-ethyl-3-methylethylcarbamoylisoxazole-4-carboxylate are obtained as a mixture of two amide rotamers.

$^1$H-NMR (CDCl$_3$; 250 MHZ) δ = 1.17 and 1.27 (2t; 2.33 3H), 1.35 (t; 3H), 2.89 and 3.12 (2s; 2.33 3H), 3.18 (q; 2H), 3.25 and 3.63 (2q; 2×2H), 3.84 (s; 3H).

Investigation of the reaction mixtures by gas chromatography before working up showed no detectable isoxazole-4-carboxamide IV in the experiments described. The amount of diamide V did not exceed 3 percent.

We claim:

1. A process for preparing 3-carbamoylisoxazole-4-carboxylic esters of the formula I where
$R^1$ is hydrogen, alkyl, cycloalkyl, phenyl or a 5- to 6-membered heterocyclic radical, it being possible for the organic radicals to carry substituents which are inert under the reaction conditions;
$R^2$ is alkyl, cycloalkyl, benzyl or $C_3$-$C_6$-alkenyl;
$R^3$ is hydrogen, alkyl or cycloalkyl and
$R^4$ is an aliphatic or cycloaliphatic radical or unsubstituted or substituted phenyl, or $R^4$ together with $R^3$ is a 4- to 7-membered alkylene chain which can be interrupted by oxygen, sulfur or N-methyl;
which comprises selective amidation at position 3 of an isoxazole-3,4-dicarboxylic diester of the formula II

where $R^{2'}$ has the same meanings as $R^2$ and is identical to or different from $R^2$, with a primary or secondary amine of the formula III $$\begin{array}{c} R^3 \\ \phantom{x} \diagdown \\ \phantom{xxx} N-H \\ \phantom{x} \diagup \\ R^4 \end{array} \qquad III$$

where $R^3$ and $R^4$ have the abovementioned meanings, in the presence or absence of a solvent.

2. A process as claimed in claim 1, wherein a primary amine III is used for the amidation.

3. A process as claimed in claim 1, wherein the amine is used in an amount of from 1 to 5 mol per mol of diester II.

4. A process as claimed in claim 1, wherein the amidation is carried out in the absence of a solvent and using an excess of amine relative to II.

5. A process as claimed in claim 1, wherein the amidation is carried out in a lower alkanol as solvent.

* * * * *